United States Patent [19]
Kanai

[11] Patent Number: 5,619,990
[45] Date of Patent: Apr. 15, 1997

[54] APPARATUS AND METHOD FOR MAKING A MEDICAL DIAGNOSIS BY DISCRIMINATING ATTRIBUTION DEGREES

[75] Inventor: Kazuyuki Kanai, Kasai, Japan

[73] Assignee: TOA Medical Electronics Co., Ltd., Hyogo-ken, Japan

[21] Appl. No.: 314,008

[22] Filed: Sep. 28, 1994

[30] Foreign Application Priority Data

Sep. 30, 1993 [JP] Japan .................................. 5-245618

[51] Int. Cl.$^6$ .................................................. A61B 5/00
[52] U.S. Cl. .................................................. 128/630
[58] Field of Search .................................. 128/630, 637, 128/638

[56] References Cited

U.S. PATENT DOCUMENTS 4,844,086  7/1989  Duffy .
5,083,571  1/1992  Prichep .

FOREIGN PATENT DOCUMENTS 0354716    8/1989  European Pat. Off. .
WO9008325  7/1990  European Pat. Off. .
2234589    6/1990  United Kingdom .

OTHER PUBLICATIONS

Kulikov, V.D. DataBase WPI May 12, 1995 p. 1 Database WPI.
Section EI, Week 8705 Derwent Publications Ltd.

S. Kitazawa et al. "The Journal Of Electronic Information And Communications Society A", vol. J 72–A, No. 1, pp. 41–48, Jan. 1989.

*Primary Examiner*—Angela D. Sykes
*Assistant Examiner*—Stephen Huang

[57] ABSTRACT

An apparatus comprises a memory for storing a characteristic pattern for each of a plurality of groups, a discriminant function defining part for selecting at random every combination of two groups of the plurality of groups stored in the memory and defining for every selected combination of two groups a two-group linear discriminant function which provides an optimal borderline bisecting the combination of two groups, a two-group discrimination result calculation part for calculating a two-group discrimination result to which a given sample is attributed for every combination of two groups using the two-group linear discriminant function defined by the discriminant function defining part, a support degree determination part for determining a support degree of the two-group discrimination result obtained by the two-group discrimination result calculation part for every combination of two-groups, and an attribution degree calculation part for calculating attribution degrees indicating to what extent the test data is attributed to each of the plurality of groups based on the two-group discrimination result and support degree for every combination of two groups.

30 Claims, 11 Drawing Sheets

FIG. 8

⟨Diagnosis through two-group discriminant analysis⟩

Database file : mda3.dat
Record No. :133    ID No.:982
Diagnosis class:5   Secondery anemia ③

```
WBC    :   4.70  [×10³/μl]
RBC    :   3.15  [×10⁶/μl]
HGB    :  10.60  [g/dl]
HCT    :  33.40  [%]
MCV    : 106.00  [fl]
MCH    :  33.60  [pg]
MCHC   :  31.70  [g/dl]
PLT    : 241.00  [×10³/μl]
RDW-SD :  68.90  [fl]
```

Support mode : Non

|  | Ki |
|---|---|
| β-Thalassemia | 0.077 |
| Iron deficiency anemia | 0.154 |
| Secondary anemia ① | 0.231 |
| Secondary anemia ② | 0.769 |
| Secondary anemia ③ | 0.846 |
| Aplastic anemia + MDS | 0.769 |
| Hemolytic anemia ① | 0.846 |
| Hemolytic anemia ② | 0.000 |
| Megaloblastic anemia | 0.462 |
| Under treatment of IDA | 0.385 |
| Umbilical cord blood | 0.615 |
| Polycythemia | 0.000 |
| Normal (adult) | 0.538 |
| Child (normal) | 0.308 |

⟨Most probable diseases (in decreasing order of probability)⟩

1  Hemolytic anemia ①   : 0.846
2  Secondary anemia ③   : 0.846
3  Aplastic anemia + MDS : 0.769

FIG. 9

⟨Diagnosis through two-group discriminant analysis⟩

Database file : mda3.dat  
Record No.:133  ID No.:982  
Diagnosis class: 5  Secondary anemia ③

```
WBC    :   4.70  [×10³/μl]
RBC    :   3.15  [×10⁶/μl]
HGB    :  10.60  [g/dl]
HCT    :  33.40  [%]
MCV    : 106.00  [fl]
MCH    :  33.60  [pg]
MCHC   :  31.70  [g/dl]
PLT    : 241.00  [×10³/μl]
RDW-SD :  68.90  [fl]
```

Support mode : Rij  
Ki

| | |
|---|---|
| β-Thalassemia | : 0.000 |
| Iron deficiency anemia | : 0.103 |
| Secondary anemia ① | : 0.036 |
| Secondary anemia ② | : 0.294 |
| Secondary anemia ③ | : 0.623 |
| Aplastic anemia + MDS | : 0.359 |
| Hemolytic anemia ① | : 0.563 |
| Hemolytic anemia ② | : 0.000 |
| Megaloblastic anemia | : 0.210 |
| Under treatment of IDA | : 0.210 |
| Umbilical cord blood | : 0.334 |
| Polycythemia | : 0.000 |
| Normal (adult) | : 0.144 |
| Child (normal) | : 0.062 |

⟨Most probable diseases (in decreasing order of probability)⟩

1  Secondary anemia ③     : 0.623  
2  Hemolytic anemia ①     : 0.563  
3  Aplastic anemia + MDS  : 0.359

FIG. 10

⟨Diagnosis through two-group discriminant analysis⟩

Database file : mda3.dat
Record No.:133   ID No.:982
Diagnosis class : 5  Secondary anemia ③

```
WBC    :   4.70  [×10³/μl]
RBC    :   3.15  [×10⁶/μl]
HGB    :  10.60  [g/dl]
HCT    :  33.40  [%]
MCV    : 106.00  [fl]
MCH    :  33.60  [pg]
MCHC   :  31.70  [g/dl]
PLT    : 241.00  [×10³/μl]
RDW-SD :  68.90  [fl]
```

Support mode : $R_{ij} \times C_{ij}$
$K_i$

| | |
|---|---|
| β–Thalassemia | : 0.000 |
| Iron deficiency anemia | : 0.098 |
| Secondary anemia ① | : 0.028 |
| Secondary anemia ② | : 0.253 |
| Secondary anemia ③ | : 0.563 |
| Aplastic anemia + MDS | : 0.351 |
| Hemolytic anemia ① | : 0.491 |
| Hemolytic anemia ② | : 0.000 |
| Megaloblastic anemia | : 0.209 |
| Under treatment of IDA | : 0.195 |
| Umbilical cord blood | : 0.328 |
| Polycythemia | : 0.000 |
| Normal (adult) | : 0.136 |
| Child (normal) | : 0.052 |

⟨Most probable diseases (in decreasing order of probability)⟩
  1  Secondary anemia ③   : 0.563
  2  Hemolytic anemia ①   : 0.491
  3  Aplastic anemia + MDS : 0.351

5,619,990

APPARATUS AND METHOD FOR MAKING A MEDICAL DIAGNOSIS BY DISCRIMINATING ATTRIBUTION DEGREES

BACKGROUND OF THE INVENTION

1. Field of the Invention

The present invention relates to an apparatus and method for making a medical diagnosis by discriminating attribution degrees for determining to which of multiple disease groups, test data of a given patient is attributed through multiple-group discriminant analysis by integrating the results of two-group linear discriminant analysis. Such an apparatus and method are useful, for example, for diagnosing diseases (or for determining to which of multiple disease groups the patient belongs).

2. Description of the Related Art

The two-group linear discriminant analysis is one of the most popular methods for statistically determining to which of two disease groups a given patient belongs. The two-group linear discriminant analysis provides a highly dense information from the viewpoint of knowledge acquisition because the two-group linear discriminant analysis allows determining to which of two disease groups the patient belongs by determining whether two group-linear discriminant function assumes a positive value or a negative value.

On the other hand, examples of approaches for determining one group out of probable multigroups with respect to given disease data (diagnosis systems) include an approach represented by an expert system by which the disease group is determined with coded information of knowledge and an inference engine, an approach using the learning of a neural network, and an approach for inductively determining the disease group in a multiple-group discriminant analysis as an application of multivariate analyses.

A process by which an experienced medical specialist, for example, selects one disease group from the rest of multiple disease groups is as follows. The medical specialist will never select one group at one time, but will rather select several probable groups from multiple disease groups to finally select the most probable group through comparison of the probable groups. In general, this process is referred to as "preferable selection process" in which humans exhibit a relatively high ability.

With respect to the recognition of multiple group patterns as mentioned above, the Journal of Electronic Information and Communications Society A, Vol.J 72-A, No.1, pp.41–48, January, 1989 discloses a multiple group pattern recognition by pair discrimination.

In this multiple group pattern recognition, two groups are discriminated from each other with respect to all pairs to produce the discrimination result for multiple groups by integrating the result of the two group discrimination. The multiple pattern recognition presumes a variance-covariance matrix not common for all groups, but separate for each of the pairs. Then the multiple pattern recognition calculates the squares $D_i^2$ and $D_j^2$ of Mahalanobis' generalized distances between an unknown input pattern x and each of two groups i and j, and posteriori probabilities $P(\Pi i|x)$ and $P(\Pi j|x)$. The two group discrimination results are obtained by a comparison between the squares $D_i^2$ and $D_j^2$ of Mahalanobis' generalized distances and between the posteriori probabilities $P(\Pi i|x)$ and $P(\Pi j|x)$. After these results are normalized (to obtain normalized pair statistics) and integrated with each other, the final discrimination result is obtained for the unknown input pattern x. However, the Journal describes no specific method for calculating the posteriori probabilities $P(\Pi i|x)$ and $P(\Pi j|x)$.

Furthermore, the Journal describes three methods for obtaining the final discrimination result, a decision by majority, a minimax method and an approach by expectation values. The decision by majority is a method in which a solution is decided by majority on integrated results of two-group discriminant analysis. The minimax approach is a method in which the maximum value of the Mahalanobis' generalized distances is calculated between the unknown pattern and group, and, the unknown pattern is excluded from the group which has the maximum value. This method is effective when the number of groups are large. The approach by expectation values is a method in which an expectation value of a normalized pair statistic is calculated for a group $\Pi i$ to decide a solution which provides the best result.

In such conventional multiple-group discriminant analysis, however, the quality of data used for knowledge acquisition (e.g., for the calculation of a linear discriminant function) often affects the reliability of the obtained linear discriminant function, for example, when a system is actually constructed for diagnosing each case of disease.

In the actual diagnosis of disease using two group discrimination discriminant analysis, some combinations of two groups are significant, while others are not. Therefore, it is not preferable to equally treat all the combinations of two groups in two-group discriminant analysis. Medical specialists seem to account for the difference in the significance of combinations of two groups based on empirical knowledge.

The foregoing points are very important for actual systems of discriminating multiple groups, especially for systems of diagnosing diseases.

SUMMARY OF THE INVENTION

The present invention has been made in view of the aforementioned circumstances, and an object of the present invention is to provide an apparatus and method for making a medical diagnosis by discriminating attribution degrees for determining to which of multiple disease groups, test data of a given sample is attributed through calculation in a two-group discriminant analysis and, at the same time, determining a support degree of the result of the two-group discriminant analysis for every combination of two groups and determining the attribution degree of to what extent the test data is attributed to each group With reference to the support degree, thereby enabling a more reliable determination of attribution degree than conventional techniques.

Therefore, the present invention provides an apparatus for making a medical diagnosis by discriminating attribution degrees, said apparatus comprising:

memory means for storing a characteristic pattern for each of a plurality of groups;

discriminant function defining means for defining for every combination of two groups of the plurality of groups stored in said memory means a two, group linear discriminant function which provides a borderline bisecting combination of two groups;

two-group discrimination result calculation means for calculating a two-group discrimination result to which a given sample may be attributed for-every combination of two groups using the two-group linear discriminant function defined by said discriminant function defining means;

support degree determination means for determining a support degree of the two-group discrimination result obtained by said two-group discrimination result calculation means for every combination of two groups; and attribution degree calculation means for calculating attribution degrees indicating to what extent the test data is attributed to each of the plurality group based on the two-group discrimination result and support degree for every combination of two groups.

In the present invention, the discriminant function defining means selects at random two groups from the multi-groups stored in the memory means, and defines a linear discriminant function which provides an optimal borderline bisecting the selected two-groups. Subsequently, the two group discrimination result calculation means obtains a two group discrimination result of which of the two groups test data of a given sample is attributed to through the calculation of the linear discriminant function, and then the support degree determination means obtains a support degree of the two-group discrimination result. This process is performed for every combination of two groups.

Finally, the attribution degree of to what extent the test data is attributed to each group is calculated, based on the obtained two-group discrimination results and support degree. This enables accurate determination of a disease group on the basis of knowledge acquisition.

BRIEF DESCRIPTION OF THE DRAWINGS

The present invention will be detailed in conjuction with the accompanying drawings, but the invention is not limited by them.

FIG. 8 is one example of a printout of a determination result obtained from an actual attribution degrees determination analysis with no support degree;

FIG. 9 is another example of a printout of a discrimination result obtained from an actual attribution degree determination analysis with a support degree determined from a distance ratio; and FIG. 10 is still another example of a printout of a discrimination result obtained from an actual attribution degree determination analysis with a support degree determined from a distance ratio and a correlation ratio.

DESCRIPTION OF THE PREFERRED EMBODIMENTS

Figure 1:
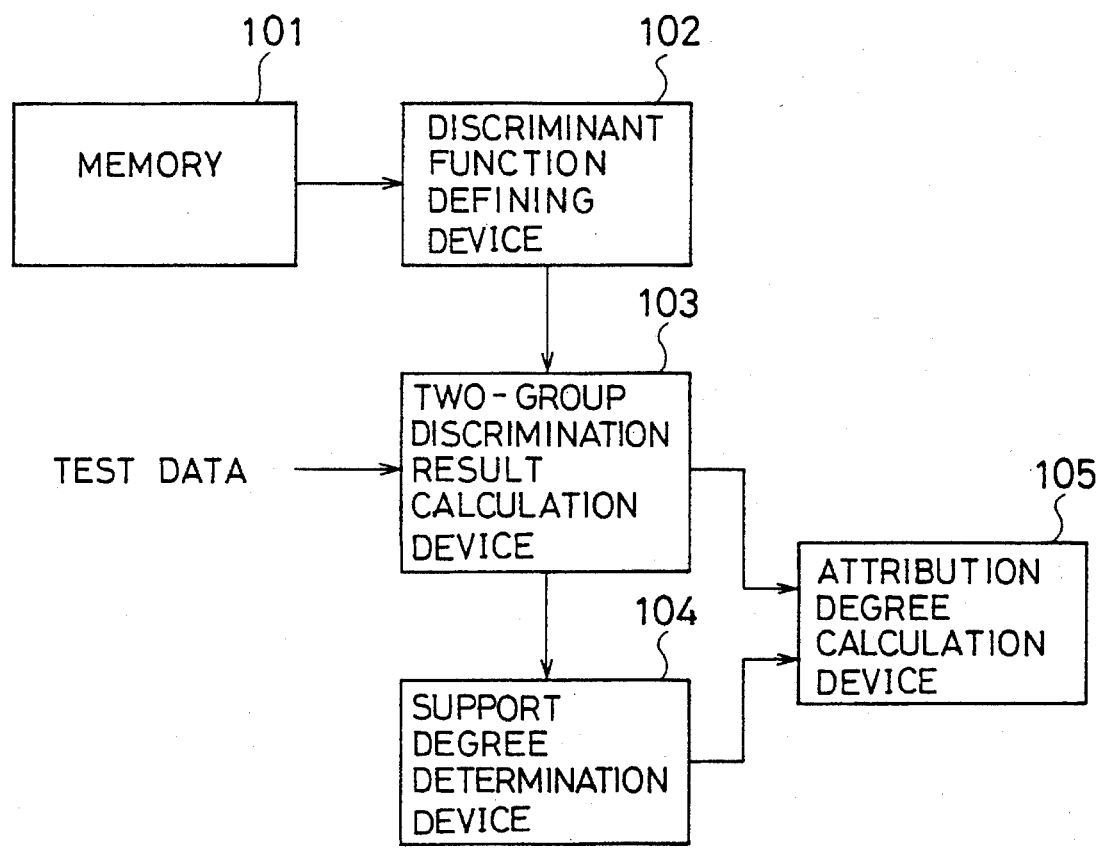
FIG. 1 is a block diagram illustrating a configuration of one embodiment of the present invention.

FIG. 1 is a block diagram showing one embodiment of the present invention. As the memory 101 in FIG. 1 according to the present invention, any type of external memory device may be used such as a floppy disk system or a magnetic disk system.

As the discriminant function defining device 102 in FIG. 1, the two group discrimination result calculation device 103, the support degree determination device 104, and the attribution degree calculation device 105 may comprise a micro-processor including a CPU, ROM, RAM, and I/O port.

In accordance with the present invention, the determination of the support degree by the support degree determination device 104 is preferably based on three factors: a quantified two-group discrimination degree which indicates whether the discrimination has been made based on a marginal difference or a large difference in the discrimination result; a quantified certainty degree of discriminant function which indicates the certainty of a two-group linear discriminant function; and a quantified significance degree which indicates the significance of a two-group combination to be discriminated.

The quantified two-group discrimination degree for the determination of the support degree by the support degree determination device 104 is preferably obtained by calculating each of the squares of Mahalanobis' generalized distances between the test data and each of two groups and the distance ratio therebetween and then normalizing the distance ratio.

Further, the quantified certainty degree of discriminant function for the determination of the support degree by the support degree determination device 104 is preferably determined by a correlation ratio which serves as an evaluation standard of a discriminant performance when a linear discriminant function is defined for each combination of the two groups by the discriminant function defining device 102.

The present invention will be hereinafter described by way of a preferred embodiment illustrated in the attached drawings, but it should be understood the present invention is not limited to this particular embodiment.

In this preferred embodiment, measured data of seven items, namely, WBC (white blood cell count), RBC (red blood cell count), HGB (hemoglobin concentration), MCV (mean corpuscular volume), MCHC (mean corpuscular hemoglobin concentration), PLT (platelet count), and RDW (red blood cell distribution width), which are obtained from a blood analyzer, are used to determine to which of 14 disease groups seven-dimensional test data X (which includes X1, X2, X3, X4, X5, X6 and X7) is attributed. The aforementioned 14 disease groups includes a β-Thalassemia group, an iron deficiency anemia group, a secondary anemia 1 group, a secondary anemia 2 group, a secondary anemia 3 group, an aplastic anemia and an MDS group, a hemolytic amenia 1 group, a hemolytic amenia 2 group, a megaloblastic anemia group, a group under treatment of iron deficiency amenia, an umbilical blood group, a polycythemia group, a normal (adult) group, and a normal (child) group.

Figure 2:
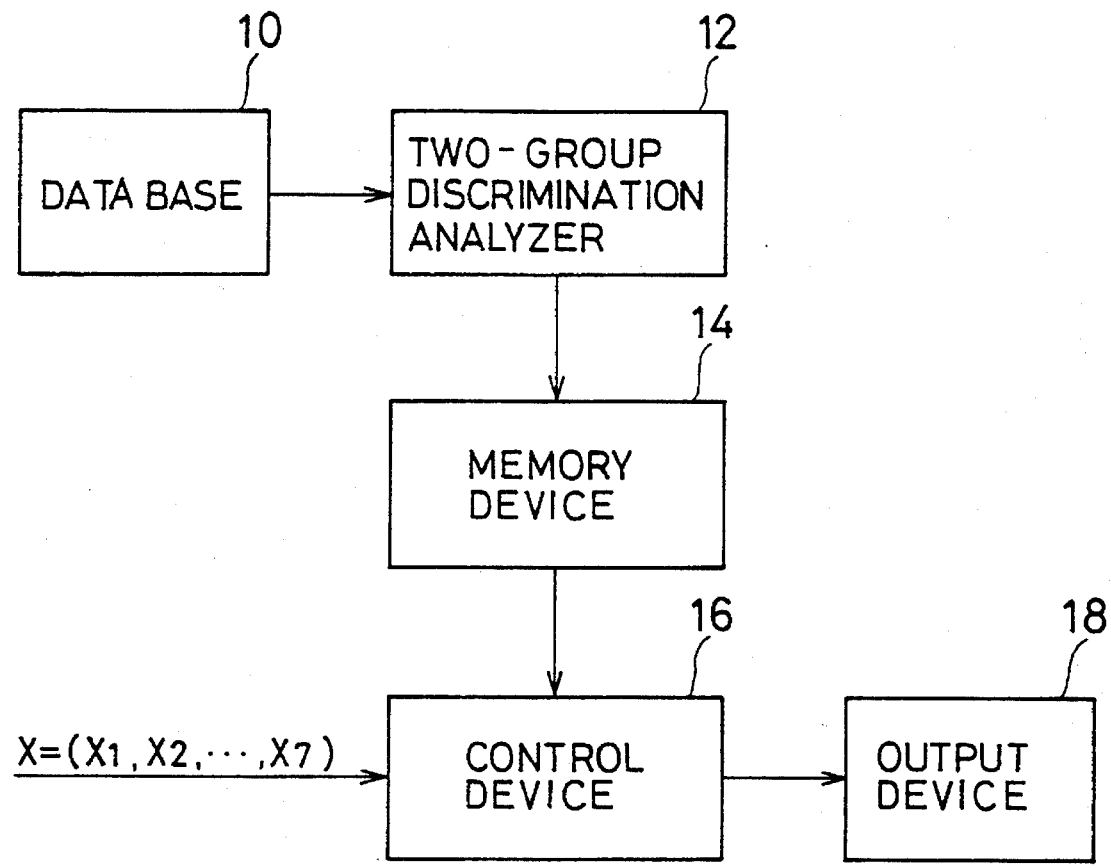
FIG. 2 is a block diagram illustrating a configuration of an apparatus for discriminating attribution degrees in accordance with one embodiment of the present invention.

FIG. 2 is a block diagram illustrating an apparatus for discriminating attribution degrees according to one embodiment of the present invention. The apparatus in FIG. 2 includes database 10 including an external storage device such as a floppy disk system or magnetic disk system, a two-group discriminant analyzer 12, a memory device 14, such as RAM or the like, a control device 16, and an output device 18 including a display device such as CRT display and/or a printer device such as dot printer. The two-group discriminant analyzer 12 and the control device 16 comprise a micro-processor having a CPU, ROM, RAM and I/O port.

Figure 3:
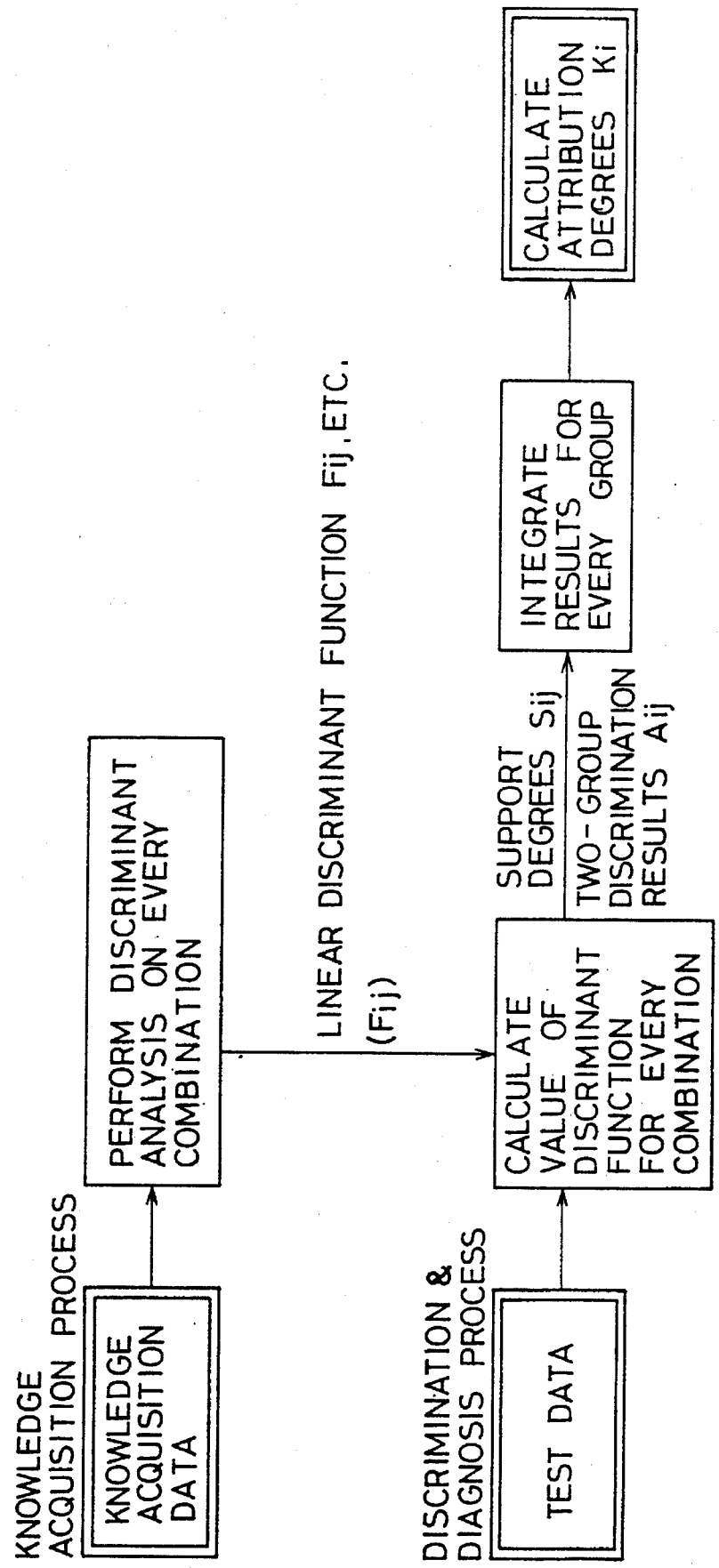
FIG. 3 is a block diagram illustrating process steps for discriminating attribution degrees according to the present invention;.

FIG. 3 is a block diagram illustrating general processing steps for discriminating attribution degrees according to the present invention. Referring to FIG. 3, the processing steps will be hereinafter described.

First, reference is made to knowledge acquisition of process. To determine the attribution degree by the present invention, it is prerequisite to prepare a number of items of high-quality knowledge acquisition data Di (i=1 to 14) for each of the aforementioned disease groups i (i=1 to 14).

This knowledge acquisition data group Di includes seven items of blood data, namely, WBC, RBC, HGB, MCV, MCHC, PLT and RDW, obtained from actual blood analysis in which blood samples have been taken from individuals who each belong to one of 14 groups of the β-Thalassemia group, the iron deficiency anemia group, the secondary anemia 1 group, the secondary anemia 2 group, the secondary anemia 3 group, the aplastic anemia and MDS group, the hemolytic amenia 1 group, the hemolytic amenia 2 group, the megaloblastic anemia group, the group under treatment of iron deficiency amenia, the umbilical blood group, the polycythemia group, the normal (adult) group, and the normal (child) group. This knowledge acquisition data group Di is stored in the database 10.

The two-group discriminant analyzer 12 reads the knowledge acquisition data Di out of the database 10, performs a two-group discriminant analysis on every combination of two groups, and then acquires knowledge such as a linear discriminant function Fij. The acquired knowledge is stored in the memory device 14.

Next, discrimination and diagnosis process will be described. The control device 16 receives unknown test data x, and quantifies the probability that the test data X would be attributed to each of the disease groups, based on the test data X and the acquired knowledge. The probability is expressed as a two-group discrimination result Aij and corresponding support degree Sij. This test data X includes seven kinds of data, i.e., WBC, RBC, HGB, MCV, MCHC, PLT and RDW, of blood sampled from a patient whose disease is to be analyzed as to which group the disease belongs.

The quantified results which each indicate the probability that the test data belongs to each of the disease groups are collected and classified into each disease group, and then attribution degree Ki are output to the output device 18. In this embodiment, a disease is identified based on the unknown test data X and the aforementioned acquired knowledge.

Figure 4:
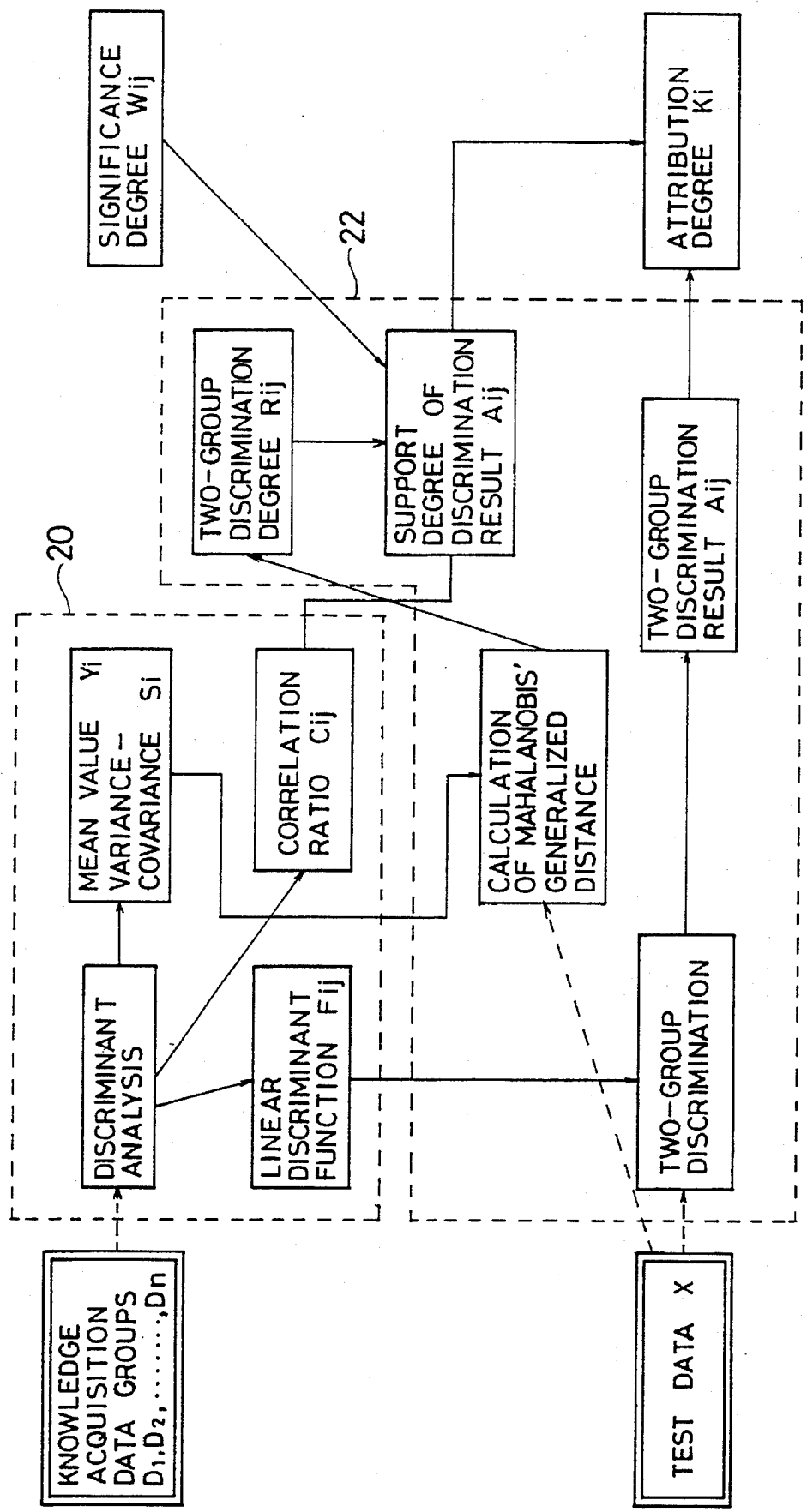
FIG. 4 is a block diagram illustrating the details of a knowledge acquisition process and a determination and diagnosis process.

FIG. 4 is a block diagram illustrating the aforementioned knowledge acquisition process and discrimination and diagnosis process in detail. In FIG. 4, the knowledge acquisition process and the determination and diagnosis process are shown in blocks 20 and 22, respectively. With reference to the block diagram shown in FIG. 4, the processing steps of the apparatus according to the present invention will be hereinafter described in detail.

The two-group discriminant analyzer 12 performs two-group linear discriminant analysis for all the combinations of two groups selected out of knowledge acquisition data D1 to D14 (14 groups). The number of the combinations of two groups (i,j) is $_{14}C_2=(14\times13)/2=91$ in all. Accordingly, it is necessary to obtain 91 linear discriminant functions Fij(X1, X2, . . . ,X7) which each provide a borderline between two groups corresponding to a combination of two groups (i,j).

The linear discriminant function Fij(X1,X2, . . . ,7X) is expressed as follows:

$$Fij(X1,X2,\ldots,X7)=aij_0+aij_1 X1+aij_2 X2+\ldots+aij_7 X7 \quad \text{Eq.(1)}$$

where, $aij_0$, $aij_1$, $aij_2$, . . . , $aij_7$ are coefficients, and X1, X2, . . . , X7 are variates.

A known method can be employed to obtain the linear discriminant function Fij(X1,X2, . . . ,X7) for best determining the disease groups Di and Dj in the knowledge acquisition data, i.e., to obtaining the aforementioned coefficients $aij_0$, $aij_1$, $aij_2$, . . . , $aij_7$. The methods of obtaining mean value matrixes Yi and Yj, variance-covariance matrixes Si and Sj, and a correlation ratio for the disease groups Di and Dj in the knowledge acquisition data are also known. These matrices Yi, Yj, Si and Sj are used to calculate the squares Mi and Mj of Mahalanobis' generalized distances between the test data X and the respective disease groups i and j, which will be described later.

The coefficients $aij_0$, $aij_1$, $aij_2$, . . . , $aij_7$ of the linear discriminant functions, mean value matrices Yi and Yj, variance-covariance matrices Si and Sj, and correlation ratio are later used as acquired knowledge by the apparatus of the present invention.

The control device 16 quantifies the probability that the test data X would be attributed to each of the disease groups, based on the test data X and the acquired knowledge. That is, the control device 16 selects a combination of two groups (i,j) out of disease groups, and determines to which disease group i or j the test data X is attributed through the calculation of a linear discriminant function Fij(X1,X2, . . . ,X7) corresponding to the selected combination of two groups. In this case, it is assumed that, if the test data X is judged to be attributed to the disease group i, Aij=1 and, if the test data X is judged to be attributed to the disease group j, Aij=0. The two-group discrimination result Aij can be determined by whether the value of a discriminant function is positive or negative, said value being obtained by substituting the test data Xi (i=1 to 7) into the aforementioned equation (1).

Though a probability degree Ki of the attribution to a disease group i could be obtained by using only such information as the aforesaid two-group discrimination result Aij, this approach is less accurate in general. That is because this technique does not take into account whether the discrimination is made based on a marginal difference or on a large difference in the discrimination result.

In view of this shortcoming, the present invention has introduced a concept of a support degree Sij of each of the two-group discrimination results for groups i and j so that the discrimination degree of the two-group discrimination results can be taken into consideration. The support degree Sij of the two-group discrimination results indicates the level of the two-group discrimination results and is expressed as a value between 0 and 1. The closer the support degree Sij approaches 1, the more the two-group discrimination result is supported, which means that the discrimination has been made based on a large difference in the discrimination result. The closer the support degree Sij approaches 0, the less the two-group discrimination result is supported, which means that the discrimination has been made based on a marginal difference in the discrimination result.

A specific example of the calculation of the support degree Sij of a two-group discrimination result is as follows, wherein a certainty degree Cij, significance degree Wij and two-group discrimination degree Rij are separately detailed.

(1) Calculation of certainty degree Cij of discriminant function.

The discriminant functions are profoundly influenced by the quality of the knowledge acquisition data of each group, because the acquisition of the discriminant function is, of course, based on actual data. In the two-group discriminant analysis, a correlation ratio may be employed to express the discriminant performance of the obtained two-group linear discriminant function Fij(X1,X2, . . . ,X7).

To calculate the correlation ratio, the frequency distributions of discriminant function values Z are obtained for two groups i and j, which discrimination function values Z are obtained by substituting the test data X into the linear discriminant functions for discriminating the two groups i and j, and the mean values Yi, Yj and variances $\sigma_i^2$, $\sigma_j^2$ (the number of samples: ni, nj) of the discriminant function values for the respective groups as well as the mean value $Y_T$ and variance $\sigma_T^2$ (the number of samples: $n_T$ (=ni+nj)) for both groups are calculated.

An intraclass variance $\sigma_W^2$ is expressed as follows:

$$\sigma_W^2 = (ni\sigma_i^2 + nj\sigma_j^2)/n_T$$

An interclass variance $\sigma_B^2$ is expressed as follows:

$$\sigma_B^2 = (ni(Y_i-Y_T)^2 + nj(Y_j-Y_T)^2)/n_T$$

Since the variance for both groups is expressed as $\sigma_T^2 = \sigma_W^2 + \sigma_B^2$, the correlation ratio Cij is calculated as follows:

$$Cij = \sigma_B^2/\sigma_T^2 \ (0 < \text{correlation ratio} < 1)$$

If the discrimination ability is high, the interclass variance is large and the intraclass variance is small. Accordingly, the correlation ratio approaches 1. The correlation ratio Cij is referred to as the certainty degree of discriminant function in this embodiment.

(2) Determination of significance degree Wij.

The attribution degree of the test data X to the group i is determined as a result of two-group linear discriminant analysis between the group i and each of the other 13 groups. When the attribution degree to the group i is calculated, there generally exists a difference in significance among these 13 combinations of two groups (in this embodiment, 13 combinations of two groups for a given group). For example, when the attribution degree to the iron deficiency anemia (IDA) group is calculated, the discrimination between the IDA group and other analogous groups such as β-Thalassemia and normal groups has a clinical significance. On the other hand, the discrimination from such disease groups as the polycythemia group is not so valuable information, and is clinically less important. In view of this, each of these 13 combinations of two groups is assigned a significance degree Wij on a maximum scale of 13 points (since there are 13 combinations of two groups for a given group according to this embodiment).

(3) Calculation of two-group discrimination degree Rij.

The squares Mi and Mj of Mahalanobis' generalized distances between the test data X and each of the disease groups i and j are calculated.

As is well known, the square Mi of Mahalanobis' generalized distance between the test data X and the disease group i is calculated from the following equation using the mean value matrix Yi and variance-covariance matrix Si of the disease group i obtained through the knowledge acquisition.

$$Mi = {}^t(X-Yi)Si^{-1}(X-Yi)$$

where $^t$ and $^{-1}$ mean a transposed matrix and an inverse matrix, respectively.

The square Mj of Mahalanobis' generalized distance between the test data X and the disease group j is calculated in the same manner.

From these two squares Mi and Mj of Mahalanobis' generalized distances, the ratio MRij of Mj to Mi is calculated, and then a two-group discrimination degree Rij is calculated, for example, from the following function f(x) to convert MRij into a value between 0 and 1.
where MRij(=Mj/Mi) is as "x".

$$Rij = f(x) \frac{1 - \exp(-0.366 \times (x-1))}{1 + \exp(-0.366 \times (x-1))}$$

if x<1, then Rij=0.

Figure 5:
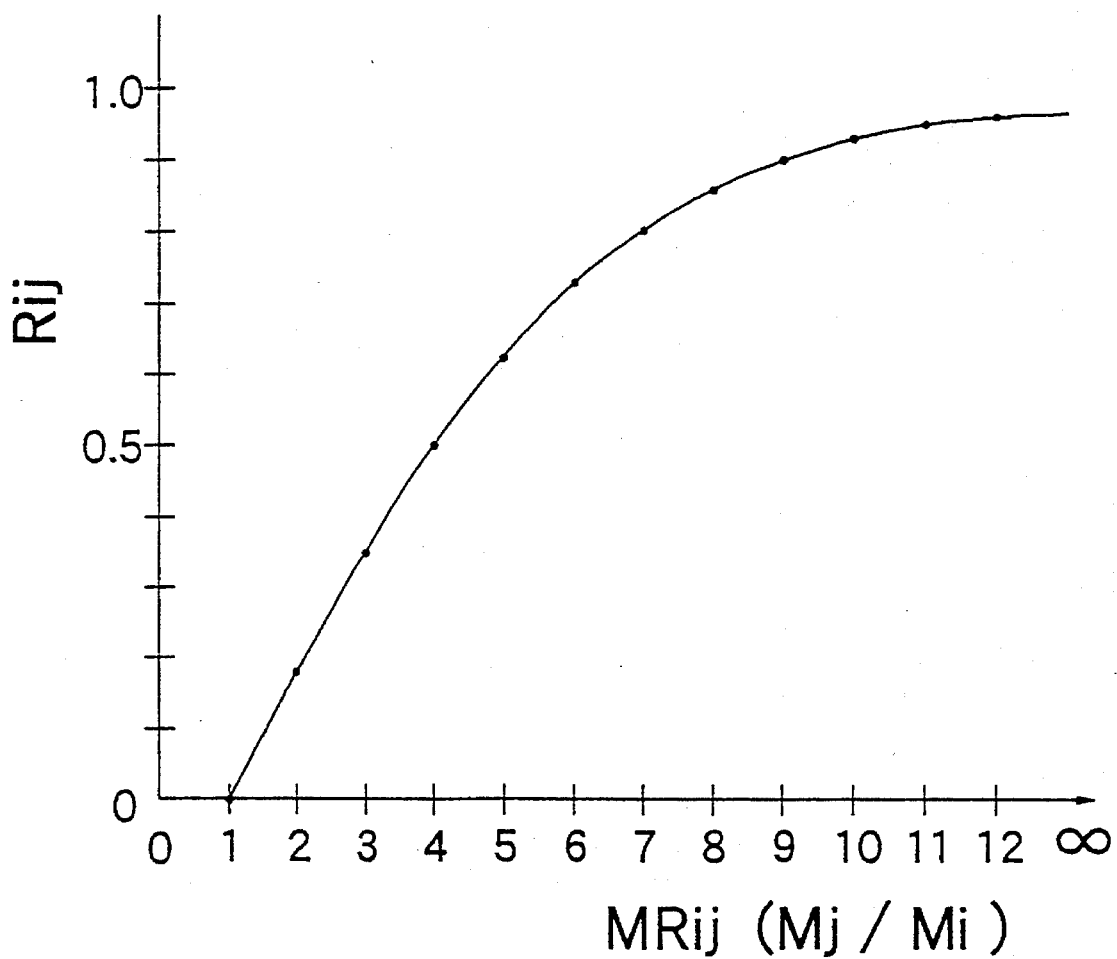
FIG. 5 is a graphic representation illustrating a function f(x) of two-group discrimination degree Rij.

FIG. 5 is a graphic representation showing the function f(x). The function f(x) is one example of a continuous function for normalization by which MRij having a value of 1 to ∞ can be successively converted into a value between 0 and 1.

The coefficient −0.366 is specified so that the function f(x) satisfies the condition in which, when Rij=4, i.e., the ratio of Mahalanobis' generalized distance between the test data X and the group j to that between the test data X and the group i is 2, the value of the two-group discrimination degree Rij is 0.5. It is necessary to change the coefficient depending on the relative closeness between two groups to be discriminated.

Another calculation method is to employ a hitting ratio of the discrimination obtained when a two-group linear discriminant is applied to the knowledge acquisition data.

Using the foregoing certainty degree Cij of discriminant function, significance degree Wij, and two-group discrimination degree Rij, the support degree Sij is calculated as follows:

$$Sij = Rij \times Cij \times Wij$$

and then the attribution degree Ki to the group i is calculated from the following equation:

$$Ki = \sum_{j=1}^{n} Aij \times Sij \times 1/(n-1)$$

where n=14, and j≠i. When it has been judged the test data X is attributed to the group i, Aij=1, and when it has been judged that the test data X is attributed to the group j, Aij=0. The value of the attribution degree Ki is between 0 and 1 (0≦Ki≦1).

Even by taking into consideration the two-group discrimination degree Rij alone, the discrimination accuracy may be improved, compared with a conventional approach. By introducing the certainty degree Cij of discriminant function to the support degree Sij (Sij=Rij×Cij), the discrimination result becomes more conformable to the actual knowledge acquisition data.

By further introducing the significance degree Wij to the support degree Sij (Sij=Rij×Cij×Wij), the discrimination result becomes closer to that obtained through human judgement.

Next, the processing operations will be hereinafter described with reference to the flow charts shown in FIGS. 6 and 7.

Figure 6:
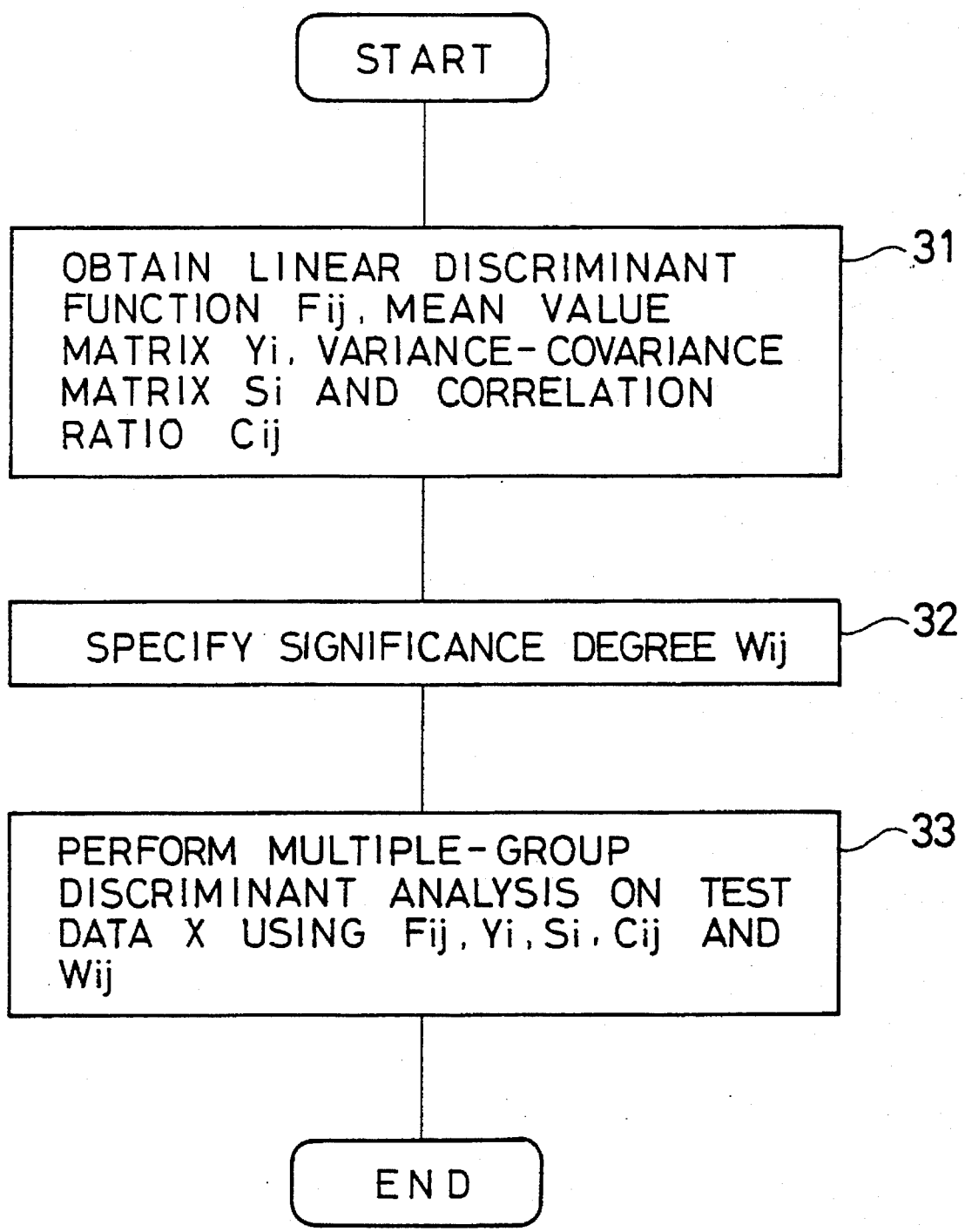
FIG. 6 is a flow chart illustrating comprehensive processing steps in the knowledge acquisition process, and determination and diagnosis process.

FIG. 6 is a flow chart illustrating the comprehensive processing steps of the knowledge acquisition process and discrimination & diagnosis process.

According to the process flow of the apparatus of the present invention, a linear discriminant function Fij, mean value matrix Yi, variance-covariance matrix Si, and correlation ratio Cij are obtained for each combination of two groups from a knowledge acquisition data group Di at Step 31 of the knowledge acquisition process. At Step 32, a significance degree Wij is specified for each of the two-group combinations. The significance degree Wij may be preliminarily specified along with the knowledge acquisition data group Di.

At Step 33 of the discrimination & diagnosis process, a multiple-group discriminant analysis is performed on test data X, using the linear discriminant function Fij, mean value matrix Yi, variance-covariance matrix Si, correlation ratio Cij, and significance degree Wij.

Figure 7A:
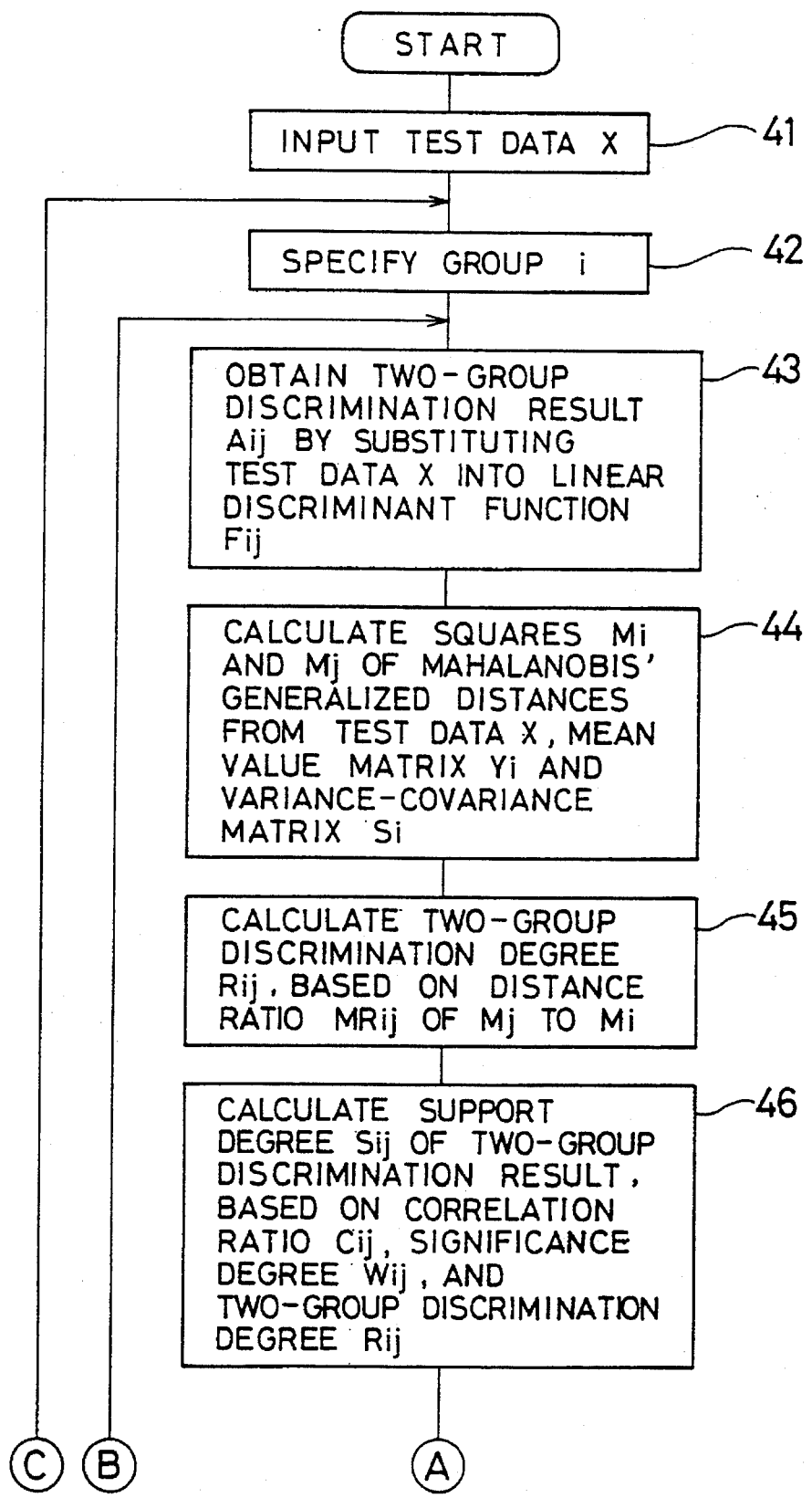
FIG. 7(a) and 7(b) are a flow chart illustrating the details of the processing steps of the determination and diagnosis process.
Figure 7B:
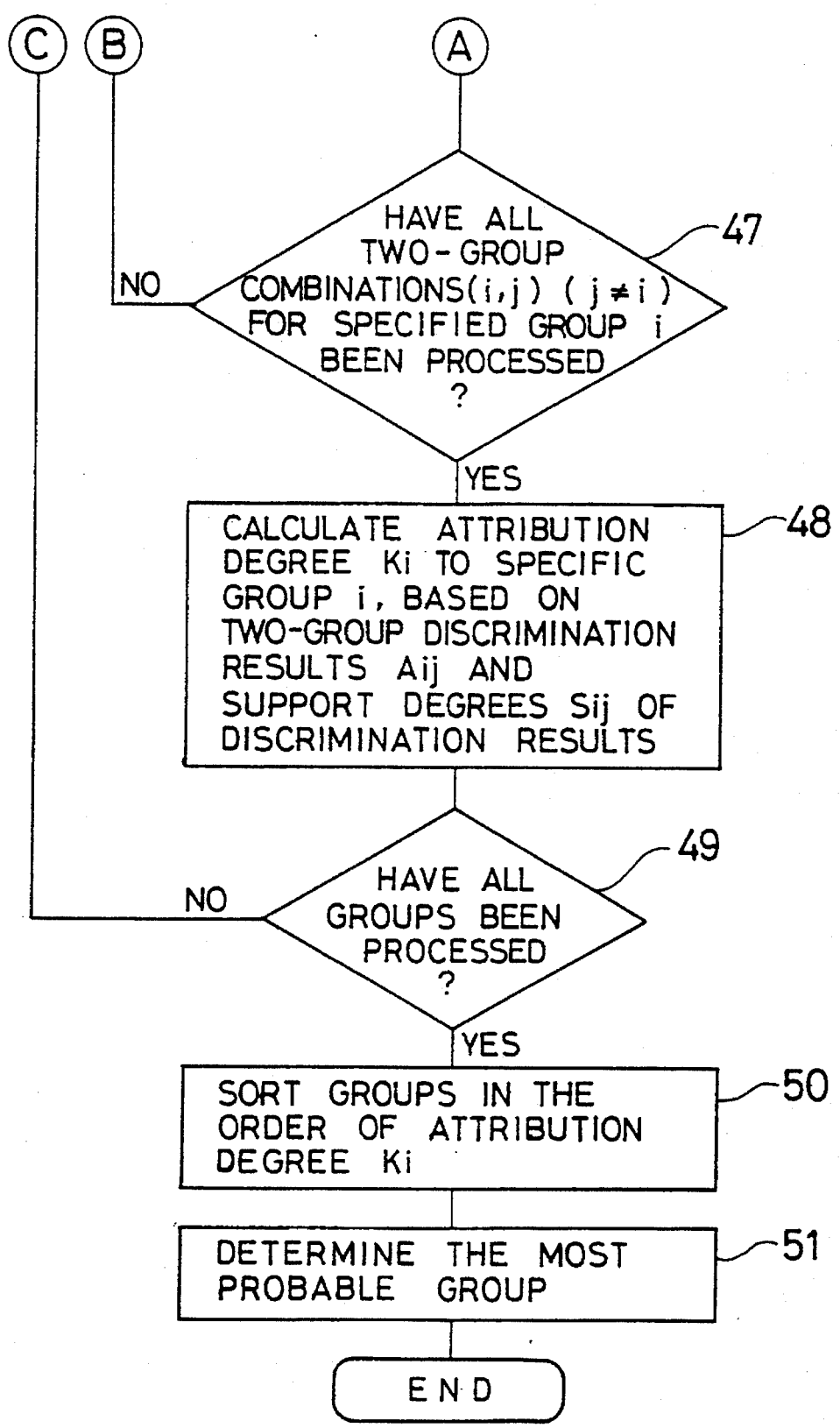

FIG. 7(a) and 7(b) are a flow chart illustrating the details of the discrimination and diagnosis process.

In the determination and diagnosis process, test data X is input at Step 41, and then any group i is specified at Step 42. A two-group discrimination result Aij is determined by substituting the test data X into the linear discriminant function Fij at Step 43.

At Step 44, Mahalanobis' generalized distances Mi and Mj are calculated from the test data X, mean value matrix Yi and variance-covariance matrix Si. At Step 45, a two-group discrimination degree Rij is calculated, based on the ratio MRij of squares of Mahalanobis' generalized distances Mi and Mj.

At Step 46, a support degree Sij of the two-group discrimination result Aij is calculated from the correlation ratio Cij, significance degree Wij and two-group discrimination degree Rij.

At Step 47, it is checked whether all the combinations of two groups ij (j≠i) for the specified group i have been processed. If the answer is "no", the process returns to Step 43, and Steps 43 to 47 are repeated until all the combinations of two groups have been processed. If the answer is "yes", an atttibution degrees Ki for the specified group i is calculated from the two-group discriminant results Aij and the support degree Sij of the two-group discrimination results Aij at Step 48.

At Step 49, it is checked whether all groups i have been processed. If the answer is "no", the process returns to Step 42, and Steps 42 to 49 are repeated until all the groups have been processed. If the answer is "yes", the groups are sorted in the reducing order of the atttibution degrees Ki at Step 50, and the most probable group i is identified at Step 51.

FIGS. 8 to 10 each show an example of printout of a discrimination result obtained through an actual implementation of the aforesaid process.

In this implementation, the test data was obtained from a specimen sampled from a patient contracting secondary anemia 3, and an atttibution degrees Ki was obtained for each of the disease groups using the above-identified process.

The discrimination result shown in FIG. 8 was obtained in a mode which took into account Only two-group discrimination result Aij, but not the support degree Sij of the two-group discrimination result (Support Mode: None). The discrimination result shown in FIG. 9 was obtained in a mode which took into account the two-group discrimination degree Rij as the support degree Sij of two-group discrimination result (Support Mode: Distance Ratio). The discrimination result shown in FIG. 10 was obtained in a mode which took into account the two-group discrimination degree Rij and the certainty degree Cij of discriminant function as the support degree Sij of two-group discrimination result (Support Mode: Distance Ratio and Correlation Ratio).

The atttibution degrees Ki in each of the modes is calculated as follows:

[Support Mode: None]

$$Ki = \sum_{j=1}^{n} Aij \times 1/(n-1) \text{ (on condition } j \neq i)$$

[Support Mode: Distance Ratio]

$$Ki = \sum_{j=1}^{n} Aij \times Rij \times 1/(n-1) \text{ (on condition } j \neq i)$$

[Support Mode: Distance Ratio & Correlation Ratio]

$$Ki = \sum_{j=1}^{n} Aij \times Rij \times Cij \times 1/(n-1) \text{ (on condition } j \neq i)$$

When the support degree Sij of two-group discrimination result was not taken into consideration, the atttibution degree Ki of the secondary anemia 3 group and hemolytic anemia 1 group were the same, as shown in FIG. 8. However, when the two-group discrimination degree Rij was taken into consideration as the support degree Sij of the two-group discrimination result as shown in FIG. 9, and when the two-group discrimination degree Rij and the certainty degree Cij of the discrimination function were both taken into consideration as shown in FIG. 10, the atttibution degree Ki of the secondary anemia 3 group ranked first.

Furthermore, in comparison of the two cases shown in FIGS. 9 and 10, the case where the certainty degree Cij of linear discriminant function was taken into account as the support degree Sij (FIG. 10) showed a larger difference in the atttibution degrees Ki between the first and second places.

According to this embodiment of the present invention, two-group discriminant analysis are performed on all the combinations of two groups selected from the knowledge acquisition data groups D1, D2, . . . , Dn to obtain two-group discriminant functions Fij which are each utilized as knowledge later. Subsequently, two-group discriminant analysis for unknown test data X are performed on all the combinations of two groups using the discriminant functions Fij to obtain two-group discrimination results Aij and support degree Sij, and then the atttibution degree Ki of the test data to all groups are calculated from the two-group discrimination results Aij and support degree Sij. Therefore, it is possible to realize an accurate identification of a disease group which conforms to the actual acquired knowledge.

As has been described, the apparatus for discriminating atttibution degrees of the present invention randomly selects a two-group combination from multiple groups, defines a linear discriminant function which provides an optimal borderline bisecting the selected two groups, obtains a two-group discrimination result indicating to which of the two groups test data of a sample is attributed using the linear discriminant function, then obtains a support degree of two-group discrimination result, and calculates the atttibution degrees of the test data for each of the groups. Therefore, the apparatus of the present invention enables an accurate identification of a disease group which is conformable to the actual acquired knowledge.

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. An apparatus for analyzing a plurality of blood samples to determine a most probable disease from one of a plurality of diseases for each of the plurality of blood samples by discriminating attribution degrees, said apparatus comprising:

input means for inputting blood sample test data, including a plurality of blood parameters for each of the plurality of blood samples, memory means for storing a plurality of characteristic values for each of the plurality of diseases;

discriminant function defining means for defining for every combination of two diseases of the plurality of diseases stored in said memory means a two-disease linear discriminant function which provides a borderline, bisecting each combination of two diseases;

two-disease discrimination result calculation means for calculating a two-disease discrimination result to which each of the plurality of blood samples may be attributed for each combination of two diseases using the two-disease linear discriminant function defined by said discriminant function defining means;

support degree determination means for determining a support degree of the two-disease discrimination result obtained by said two-disease discrimination result calculation means for each combination of two diseases; and attribution degree calculation means for calculating attribution degrees indicating to what extent on the blood sample test data is attributed to each of the plurality of diseases, based on the two-disease discrimination result and support degree for each combination of two diseases, in order to determine the most probable disease for each of the plurality of blood samples.

2. The apparatus of claim 1, wherein the support degree is determined based on a quantified two-disease discrimination degree Rij which indicates whether the two-disease discrimination result is based on a marginal difference or a large difference; a quantified certainty degree Cij of a discriminant function which indicates a certainty of the two-disease linear discriminant function; and a quantified significance degree Wij which indicates a significance of a two-disease combination to be discriminated.

3. The apparatus of claim 2, wherein the two-disease discrimination degree for determining the support degree by said support degree determination means is obtained by calculating squares of Mahalanobis' generalized distances between the blood samples test data and each combination of two diseases and a distance ratio therebetween, and normalizing the distance ratio.

4. The apparatus of claim 2, wherein the certainty degree of the two-disease linear discriminant function determining the support degree by said support degree determination means is determined by a correlation ratio which serves as an evaluation standard of a discriminant performance when a two-disease linear discriminant function is defined for each combination of two-diseases by said discriminant function defining means.

5. A method of analyzing a plurality of blood samples to determine a most probable disease from one of a plurality of diseases, for each of the plurality of blood samples, comprising the steps of:

(a) inputting blood sample test data, including a plurality of blood parameters for each of the plurality of blood samples;

(b) storing a plurality of characteristic values for each of the plurality of diseases;

(c) defining for every combination of two diseases of the plurality of diseases stored in said step (a), a two-disease linear discriminant function which provides a borderline, bisecting each combination of two diseases;

(d) calculating a two-disease discrimination result to which each of the plurality of blood samples may be attributed for each combination of two diseases using the two-disease linear discriminant function defined in said step (c);

(e) determining a support degree of the two-disease discrimination result obtained in said step (d) for each combination of two diseases; and (f) calculating attribution degrees indicating to what extent the blood sample test data is attributed to each of the plurality of diseases, based on the two-disease discrimination result and support degree for each combination of two diseases in order to determine the most probable disease for each of the plurality of blood samples.

6. The method of claim 5, wherein the support degree is determined based on a quantified two-disease discrimination degree Rij which indicates whether the two-disease discrimination result is based on a marginal difference or a large difference, a quantified certainty degree Cij of a discriminant function which indicates a certainty of the two-disease linear discriminant function, and a quantified significance degree Wij which indicates a significance of a two-disease combination to be discriminated.

7. The method of claim 6, wherein the two-disease discrimination degree for determining the support degree in said step (e) is obtained by calculating squares of Mahalonobis' generalized distances between the blood sample test data and each combination of two diseases and a distance ratio therebetween, and normalizing the distance ratio.

8. The method of claim 6, wherein the certainty degree of the two-disease linear discriminant function for determining the support degree in said step (e) is determined by a correlation ratio which serves as an evaluation standard of a discriminant performance when a two-disease linear discriminant function is defined for every combination of two diseases in said step (c).

9. An apparatus for analyzing a plurality of blood samples to determine a most probable disease by discriminating attribution degrees, comprising:

input means for receiving blood sample test data, including a plurality of characteristics values for each of the plurality of blood samples;

discrimination result determining means for generating a plurality of two-disease discriminating results Aij from the blood sample test data, knowledge acquisition data for each of a plurality of potential diseases, and a linear discriminant function;

support degree determining means for determining a support degree Sij for each of the plurality of two-disease discrimination results; and attribution degree determining means for determining the attribution degree Ki from the support degree Sij for each of the plurality of two-disease discrimination results and each of the plurality of two-disease discrimination results Aij, in order to determine the most probable disease for each of the plurality of blood samples.

10. The apparatus of claim 9, said support degree determining means determining the support degree Sij based on a two-disease discrimination degree Rij.

11. The apparatus of claim 10, wherein the two-disease discrimination degree Rij is determined by;

$$Rij = \frac{1 - \exp(-0.366 \times (x-1))}{1 + \exp(-0.366 \times (x-1))}$$

where x=a ratio of Mahalanobis' generalized distances and if x<1, then Rij=0.

12. The apparatus of claim 11, wherein the support degree Sij equals the two-disease discrimination degree Rij.

13. The apparatus of claim 10, wherein the support degree Sij is further based on a certainty degree Cij of the linear discriminant function.

14. The apparatus of claim 13, wherein the certainty degree Cij of the linear discriminant function is determined by:

$$C_{ij} = \sigma_B^2/\sigma_T^2$$

where $$\sigma_T^2 = \sigma_W^2 + \sigma_B^2$$

and $\sigma_W^2$ is an intraclass variance and $\sigma_W^2$ is an interclass variance.

15. The apparatus of claim 14, wherein the support degree Sij is determined by:

$$Sij = Rij \times Cij.$$

16. The apparatus of claim 13, wherein the support degree Sij is still further based on a significance degree Wij.

17. The apparatus of claim 16, wherein the significance degree Wij is determined by ranking the plurality of diseases from 1 to n, where n is the number of diseases.

18. The apparatus of claim 17, wherein the support degree Sij is determined by:

$$Sij = Rij \times Cij \times Wij.$$

19. The apparatus of claim 9, wherein said attribution degrees are determined by:

$$Ki = \sum_{j=1}^{n} Aij \times Sij \times 1/(n-1)$$

where n=a number of the plurality of diseases; and i,j=the two diseases of the plurality of diseases and j≠i.

20. A method of analyzing a plurality of blood samples to determine a most probable disease by discriminating attribution degrees, comprising the steps of:

(a) receiving blood sample test data, including a plurality of characteristics values for each of the plurality of blood samples;

(b) generating a plurality of two-disease discrimination results Aij from the blood sample test data, knowledge acquisition data for each of a plurality of potential diseases, and a linear discriminant function;

(c) determining a support degree Sij for each of the plurality of two-disease discrimination results; and (d) determining attribution degrees Ki from the support degree Sij for each of the plurality of two-disease discrimination results and each of the plurality of two-disease discrimination results Aij, in order to determine the most probable disease for each of the plurality of blood samples.

21. The method of claim 20, said step (b) determining the support degree Sij based on a two-disease discrimination degree Rij.

22. The method of claim 21, wherein the two-disease discrimination degree Rij is determined by:

$$Rij = \frac{1 - \exp(-0.366 \times (x-1))}{1 + \exp(-0.366 \times (x-1))}$$

where x=a ratio of Mahalanobis' generalized distances and if x<1, then Rij=0.

23. The method of claim 22, wherein the support degree Sij equals the two-disease discrimination degree Rij.

24. The method of claim 21, wherein the support degree Sij is further based on a certainty degree Cij of the linear discriminant function.

25. The method of claim 24, wherein the certainty degree Cij of the linear discriminant function is determined by:

$$Cij = \sigma_B^2/\sigma_T^2$$

where $$\sigma_T^2 = \sigma_W^2 + \sigma_B^2$$

and $\sigma_W^2$ is an intraclass variance and $\sigma_B^2$ is an interclass variance.

26. The method of claim 25, wherein the support degree Sij is determined by:

$$Sij = Rij \times Cij.$$

27. The method of claim 24, wherein the support degree Sij is still further based on a significance degree Wij.

28. The method of claim 27, wherein the significance degree Wij is determined by ranking the plurality of diseases from 1 to n, where n is the number of diseases.

29. The method of claim 28, wherein the support degree Sij is determined by:

$$Sij = Rij \times Cij \times Wij.$$

30. The method of claim 20, wherein said attribution degrees are determined by:

$$Ki = \sum_{j=1}^{n} Aij \times Sij \times 1/(n-1)$$

where n=a number of the plurality of diseases; and i,j=the two diseases of the plurality of diseases and j≠i.

* * * * *